United States Patent
Mueller et al.

(10) Patent No.: US 10,620,102 B2
(45) Date of Patent: Apr. 14, 2020

(54) VISCOSITY MEASUREMENTS BASED ON TRACER DIFFUSION

(71) Applicant: Cambridge Enterprise Ltd., Cambride, Cambridgeshire (GB)

(72) Inventors: Thomas Mueller, Cambridge (GB); Tuomas Knowles, Cambridge (GB); Paolo Arosio, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 165 days.

(21) Appl. No.: 15/741,333

(22) PCT Filed: Jun. 29, 2016

(86) PCT No.: PCT/GB2016/051946
§ 371 (c)(1),
(2) Date: Jan. 2, 2018

(87) PCT Pub. No.: WO2017/001844
PCT Pub. Date: Jan. 5, 2017

(65) Prior Publication Data
US 2018/0188145 A1 Jul. 5, 2018

(30) Foreign Application Priority Data

Jul. 2, 2015 (GB) .................................. 1511651.0

(51) Int. Cl.
*G01N 11/04* (2006.01)
*G01N 15/02* (2006.01)
(Continued)

(52) U.S. Cl.
CPC ........ *G01N 11/04* (2013.01); *B01L 3/502761* (2013.01); *B01L 3/502776* (2013.01);
(Continued)

(58) Field of Classification Search
CPC .......... G01N 11/04; G01N 1/30; G01N 11/00; G01N 13/00; G01N 15/02;
(Continued)

(56) References Cited

U.S. PATENT DOCUMENTS

| | | |
|---|---|---|
| 5,948,684 A | 9/1999 | Weigl |
| 9,952,222 B2 | 4/2018 | Yates et al. |

(Continued)

FOREIGN PATENT DOCUMENTS

| | | |
|---|---|---|
| WO | 2014064438 A1 | 5/2014 |
| WO | WO 2015/071681 A1 | 5/2015 |

(Continued)

OTHER PUBLICATIONS

International Search Report received in corresponding PCT Application PCT/GB2016/051946, dated Sep. 12, 2016.

(Continued)

*Primary Examiner* — Lisa M Caputo
*Assistant Examiner* — Nigel H Plumb
(74) *Attorney, Agent, or Firm* — Wolf, Greenfield & Sacks, P.C.

(57) ABSTRACT

A method is provided for measuring the viscosity of a fluid sample. The method comprising the steps of: (ii) providing a flow of the fluid sample; (iii) providing a component flow, wherein the component flow is a flow of the fluid sample further comprising a tracer component; (iv) generating a laminar flow of the flow (ii) with the flow (iii) in a diffusion channel, such as a microfluidic diffusion channel (2); (iv) measuring the lateral diffusion of the tracer component across the flows; and (v) determining the viscosity of the fluid from the measured diffusion profile, wherein the size of the tracer component is known or is determined.

16 Claims, 7 Drawing Sheets

(51) Int. Cl.
   *B01L 3/00* (2006.01)
   *G01N 13/00* (2006.01)
   *G01N 11/00* (2006.01)
   *G01N 1/30* (2006.01)
   *G01N 33/487* (2006.01)

(52) U.S. Cl.
   CPC .............. *G01N 1/30* (2013.01); *G01N 11/00* (2013.01); *G01N 13/00* (2013.01); *G01N 15/02* (2013.01); *B01L 2300/0867* (2013.01); *B01L 2300/0883* (2013.01); *B01L 2400/0472* (2013.01); *G01N 33/487* (2013.01); *G01N 2013/003* (2013.01)

(58) Field of Classification Search
   CPC .............. G01N 2013/003; G01N 35/08; B01L 3/502761; B01L 3/502776; B01L 2300/0867; B01L 2300/0883; B01L 2400/0472; G02N 33/487
   See application file for complete search history.

(56) References Cited

U.S. PATENT DOCUMENTS

| | | | |
|---|---|---|---|
| 9,958,369 | B2 | 5/2018 | Cohen et al. |
| 10,295,545 | B2 | 5/2019 | Yates et al. |
| 10,386,332 | B2 | 8/2019 | Herling et al. |
| 2018/0188145 | A1 | 7/2018 | Mueller et al. |
| 2018/0328831 | A1 | 11/2018 | Cohen et al. |
| 2019/0201903 | A1 | 7/2019 | Douglas et al. |
| 2019/0234530 | A1 | 8/2019 | Douglas et al. |
| 2019/0247853 | A1 | 8/2019 | Douglas et al. |
| 2019/0247855 | A1 | 8/2019 | Douglas et al. |
| 2019/0331692 | A1 | 10/2019 | Yates et al. |

FOREIGN PATENT DOCUMENTS

| | | |
|---|---|---|
| WO | WO 2017/141048 A1 | 8/2017 |
| WO | WO 2017/174975 A1 | 10/2017 |
| WO | WO 2018/046952 A1 | 3/2018 |

OTHER PUBLICATIONS

Kamholz, et al.: "Quantitative Analysis of Molecular Interation in a Microfluidic Channel: The T-Sensor," Analytical Chemistry, American Chemical Society, vol. 71, No. 23, Dec. 1, 1999, pp. 5340-5347, XP000902371, ISSN: 0003-2700, DOI: 10.1021/AC990504J.

Jichul, et al.: "Brownian Microscopy for Simultaneous in Situ Measurements of the Viscosity and Velocity Fields in Steady Laminar Microchannel Flows," Journal of Microelectromechanical Systems, IEEE Service Center, US, vol. 1, No. 5, Oct. 1, 2008, pp. 1135-1143, XP011232030, ISSN: 1057-7157, DOI: 10.1109/JMEMS.2008.927746.

Goins et al., Macromolecular crowding and size effects on probe microviscosity. Biophys J. Dec. 2008;95(11):5362-73. doi: 10.1529/biophysj.108.131250. Epub Sep. 12, 2008.

He et al., High-throughput dynamic light scattering method for measuring viscosity of concentrated protein solutions. Anal Biochem. Apr. 1, 2010;399(1):141-3. doi: 10.1016/j.ab.2009.12.003. Epub Dec. 6, 2009.

Kamholz et al., Optical measurement of transverse molecular diffusion in a microchannel. Biophys J. Apr. 2001;80(4):1967-72.

Mason et al., Diffusing-wave-spectroscopy measurements of viscoelasticity of complex fluids. J Opt Soc Am A. 1997;14(1):139-49.

Palmer et al., Diffusing wave spectroscopy microrheology of actin filament networks. Biophys J. Feb. 1999;76(2):1063-71. Erratum in: Biophys J Apr. 1999;76(4):2317.

Segur et al., Viscosity of glycerol and its aqueous solutions. Ind Eng Chem. Sep. 1951;43(9):2117-20.

Tseng et al., Micromechanical mapping of live cells by multiple-particle-tracking microrheology. Biophys J. Dec. 2002;83(6):3162-76.

Valentine et al., Investigating the microenvironments of inhomogeneous soft materials with multiple particle tracking. Phys Rev E Stat Nonlin Soft Matter Phys. Dec. 2001;64(6 Pt 1):061506. Epub Nov. 21, 2001. 9 pages.

VISCOSITY MEASUREMENTS BASED ON TRACER DIFFUSION

RELATED APPLICATIONS

This Application is a national stage filing under 35 U.S.C. 371 of International Patent Application Serial No. PCT/GB2016/051946, filed Jun. 29, 2016. Foreign priority benefits are claimed under 35 U.S.C. § 119(a)-(d) or 35 U.S.C. § 365(b) of British application number 1511651.0, filed Jul. 2, 2015. The entire contents of these applications are incorporated herein by reference in their entirety.

FIELD OF THE INVENTION

The present invention relates to flow diffusion methods for determining the viscosity of a fluid sample.

BACKGROUND

The measurement of the viscosity of complex solutions is a ubiquitous problem in biological, biophysical and biotechnological sciences. In addition, viscosity plays an important part in a wide range of technological applications that are based on fluid flow.

It is desirable to measure the viscosity of a fluid sample using high-throughput techniques using low volumes of sample. Several micro-rheological approaches have been described as alternatives to conventional viscometers and rheometers.

A common strategy for determining fluid viscosity involves monitoring the diffusion motion of tracer particles of known size. The movement of a single tracer particle may be monitored by video-microscopy (see, for example, Valentine et al. and Tseng et al.). Alternatively, the motion of tracer particles may be monitored by recording fluctuations in the average light scattering or fluorescence signal of the tracer particles (see, for example, Mason et al.; He et al.; Palmer et al.; and Goins et al.). In these approaches, the viscosity of the fluid is readily quantified from the measured apparent diffusion coefficient of the tracer particle, as understood from the Stokes-Einstein relationship between viscosity and diffusion.

In diffusion wave spectroscopy (DWS) and single particle tracking, a generalized Langevin equation of motion can be applied to correlate the time evolution of the measured mean square displacement with the storage and loss moduli of the fluid (see, for example, Tseng et al. and Mason et al.).

The present invention provides alternative methods for the determination of viscosity, such as relative viscosity.

SUMMARY OF THE INVENTION

The present invention generally provides a method for determining the viscosity of a fluid sample. The method comprises the step of monitoring the diffusion of an added component of known size through the fluid sample over time. From the measured diffusion profiles it is possible to determine the viscosity of the fluid sample.

Accordingly, in a first aspect of the invention there is provided a method for determining the viscosity of a fluid sample, the method comprising the steps of:
(ii) providing a flow of the fluid sample;
(iii) providing a component flow, wherein the component flow is a flow of the fluid sample further comprising a tracer component;
(iv) generating a laminar flow of the flow (ii) with the flow (iii) in a channel, such as a microfluidic channel;
(iv) measuring the lateral diffusion of the tracer component across the flows; and
(v) determining the viscosity of the fluid from the measured diffusion profile,
wherein the size of the tracer component is known or is determined.

In an embodiment of the invention, the method further comprise the preliminary step of (i) adding a tracer component to a part of the sample fluid.

The tracer component is a component that is added to the fluid sample for the purpose of determining the viscosity of the sample.

The methods of the invention are performed in a flow device, such as a microfluidic device. The use of fluidic devices in the method of the invention provides for low cost and relatively simple instrumentation, as compared with, for example, those methods that make use of a relatively expensive auto-correlator. Furthermore, fluidic techniques can allow the use of small volume samples, and permit rapid analysis times.

The methods of the invention are insensitive to the composition of the fluid sample, and the methods are also insensitive to the size of the tracer component added to a part of the fluid sample. As shown herein, this is in contrast to viscosity methods based on dynamic light scattering, where viscosity measurements are complicated where an added tracer component is of a comparable size to other components within the fluid sample.

It follows that the methods for the invention are accordingly not restricted to the use of specific components or specific fluid samples.

Furthermore, the fluid methods of the present invention may be combined with other fluidic techniques. The fluidic devices used in the methods of the invention may be provided in fluid commutation with other fluid devices, and these devices may be integrated within a single flow chip.

In other aspects of the invention there are provided fluidic devices for use in the methods of the first aspect of the invention.

Further aspects and embodiments of the invention are discussed in further detail below.

DETAILED DESCRIPTION OF THE INVENTION

Figure 1A:
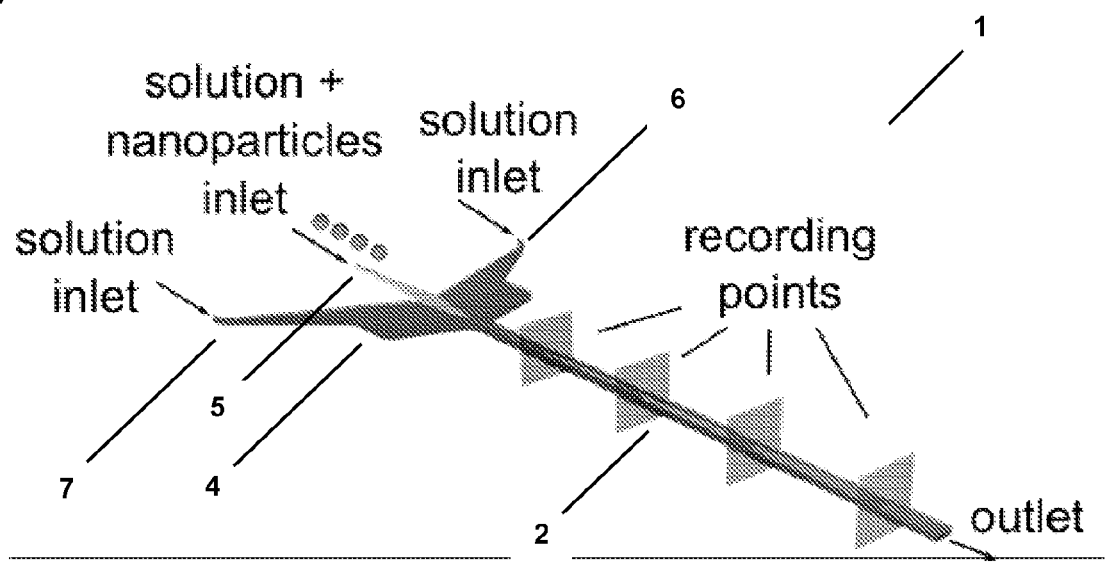
FIGS. 1a and 1b are schematics of a fluidic device for use in a diffusion method according to an embodiment of the invention.

The present invention provides a method for determining the viscosity of a fluid sample. The fluid sample for analysis is used in parts, with one part having a tracer component added to it, whilst another part is not so modified. A laminar flow of the fluid parts is generated in a channel, and the tracer component in the one part is permitted to diffuse into the other part. The movement of the tracer component over time is monitored. From the measured diffusion profiles the viscosity of the fluid sample may be determined.

The fluid flows are provided in a channel of a flow device, such as a microfluidic device. Flow devices for measuring diffusion are known in the art, and are described in further detail below.

The present inventors have previously described in WO 2014/064438 the use of diffusion techniques to analyse multicomponent mixtures. In a validation of that approach, the inventors monitored the diffusion of components having a known size. However, it is not apparent from this earlier work that the diffusion techniques could and should be used to determine the viscosity of a test sample using a tracer component.

To validate the sizing measurements, WO 2014/064438 describes the diffusion of fluorescently-labelled 25 and 100 nm polystyrene particles, separately and together, into a blank aqueous flow. The polystyrene particles are used at a concentration of 0.2% by volume. It is not apparent from this work that particles of known size and relatively low concentration could and should be added to a test sample, in order to determine the viscosity of that test sample.

The methods of WO 2014/064438 look at the movement of components out of the sample fluid flow into a blank (of buffer) fluid flow. In contrast, the methods of the present case look at the movement of a tracer component into a sample fluid flow.

Fluid Sample

The methods of the invention allow the viscosity of a fluid sample to be determined. The methods of the invention allow fluids of unknown composition to be analysed, and there is no limitation as to the nature and concentration of the components within the fluid sample.

In one embodiment, the fluid sample is a fluid sample whose viscosity is unknown.

The fluid sample may be a liquid sample.

In the methods of the invention, the fluid sample is provided in at least two parts. The first part of the fluid sample is a part having a tracer component. This tracer component may be added to the fluid sample prior to the analysis. The other part is fluid sample that does not contain the tracer component. In the methods of the invention flows of these parts of the fluid sample are brought into contact to form a laminar flow. The component is then permitted to diffuse from the flow of the first part to the flow of the other part.

A reference to a sample flow is a reference to a fluid flow of a part of the fluid sample that does not contain the tracer component.

A reference to a tracer component flow is a reference to a fluid flow of a part of the fluid sample that does contain the tracer component.

Thus, the composition of the sample flow and the tracer component flow may be identical save for the presence of the tracer component in the tracer component flow. Thus, a reference to the properties of the sample flow may be taken as a reference to the tracer component flow, as context dictates.

The sample fluid may have within it, either dissolved or dispersed, one or more components. Such components include biological molecules, and the components may contain polypeptide, polysaccharide or polynucleotide groups.

For example, a component in the sample fluid may be a protein, including an antibody.

In one embodiment, the sample fluid contains a plurality of components. It follows that the diffusion measurements follow the movement of the tracer component across multicomponent flows. In one embodiment, the fluid sample is a multicomponent mixture.

In one embodiment, the composition of the sample fluid or the concentration of components within the fluid may be unknown.

When the tracer component is provided in a part of the fluid sample this tracer component is in addition to the components within the fluid sample.

The fluid sample may contain a component having a molecular weight, such as a weight average molecular weight, of at least 300 Da, 500 Da, at least 1,000 Da (1 kDa), or at least 2 kDa.

The fluid may contain a component having a molecular weight, such as a weight average molecular weight, of at most 5 kDa, at most 10 kDa, at most 20 kDa, at most 50 kDa or at most 100 kDa.

For example, as noted above, the sample fluid may contain one or more proteins.

The fluid sample may contain (or may be suspected to contain) components that are of a similar size to the tracer component. The inventors have found that the fluid techniques of the invention allow viscosity to be determined regardless of the size of the tracer component, and regardless of the size of components that are present within the fluid sample. Thus, the methods of the invention may be used to determine the viscosity of a fluid sample having a complex and/or unknown composition.

The present inventors have found that previously described dynamic light scattering methods for determining viscosity are problematic where an added tracer component has a similar size to one or more components within the fluid sample. In particular, the convolution of the light scattering signals from the tracer component and the similarly-sized components in the fluid sample do not permit accurate sizing of the tracer particles, therefore resulting in an inaccurate viscosity determination. This is shown in the worked examples of the present case.

Given that the results from the dynamic light scattering experiments may not always be reliable, it may be necessary to repeat the dynamic light scattering experiments using tracer components of varying size in order to validate the calculated viscosity values. Alternatively it may be necessary to increase the intensity of the light scattering signal in some other way, such as increasing the concentration of the tracer components within the fluid sample. However, this latter approach is not often desirable, as the addition of a significant amount of the tracer component is likely to cause a change in the viscosity of the sample.

A reference to the size of a component in the fluid sample may be a reference to the radius, such as the hydrodynamic radius, of the component. The size of the components may be determined using standard analytical techniques. For example, diffusion measurements may be used to determine the size of components within the fluid sample.

A component present in a fluid sample may have a radius of at least 0.05 nm, at least 0.1 nm, at least 0.5 nm, at least 1 nm, or at least 5 nm.

A component present in a fluid sample may have a radius of at most 10 nm, at most 15 nm, at most 25 nm, at most 50 nm, at most 100 nm, or at most 200 nm, or at most 500 nm.

A component may have a radius in a range with upper and lower limits selected from those given above. For example, the present invention is particularly suitable for determining the viscosity of fluid samples holding components having radii in the range 0.5 to 500 nm, such as 0.5 to 200 nm, such as 0.5 to 100 nm, such as 0.5 to 15 nm.

Typically, the fluid sample is an aqueous fluid. An aqueous fluid may additionally comprise a miscible organic solvent. This may be provided to retain components in solution or suspension. For example, DMSO may be present together with water.

In the methods of the invention a tracer component-containing fluid is prepared from the fluid sample, by the addition of the tracer component into a part of the fluid sample. A further part of the fluid sample is provided, and this part does not contain the tracer component. This further part is used to generate the sample flow.

A part of the fluid sample containing the tracer component may be prepared by simple admixture of the tracer component with a part of the fluid sample.

The tracer component may be used at relatively low concentrations. The detection methods for use in the present invention, such as fluorescent detection, allow for the detection of the tracer component at very low concentrations.

The tracer component is added to the fluid sample at a level sufficient to substantially maintain the viscosity of the fluid. Thus, the viscosity of the sample flow and the tracer component flow are substantially the same, if not the same.

The determined viscosity values for the sample fluid will not be sufficiently accurate if there is a large difference in the viscosity of the sample fluid and the tracer component fluid.

The tracer component is provided in an amount sufficient to allow for its detection in the fluid flows. The minimum amount of tracer component that may be used will depend upon the analytical properties of the tracer component, such as the fluorescence efficiency tracer component, and the detection efficiency of the detector that is used.

The tracer component may be provided in a part of the fluid sample at a concentration of at least 0.001, at least 0.005, or at least 0.01 wt %.

The tracer component may be provided in a part of the fluid sample at a concentration of at most 0.05, at most 0.1, at most 0.2, at most 0.5, or at most 1.0 wt %.

The tracer component may be used at a concentration that is selected from a range having upper and lower limits selected from the values given above. For example, the tracer component may be provided in a part of the fluid sample at a concentration in the range 0.01 to 0.05 wt %.

The fluid sample may contain one or more components, and these components will also be present in the tracer component flow. The concentration of these components in the tracer component flow is substantially the same as those components within the sample flow.

Thus, the addition of the tracer component to a part of the fluid sample is not associated with a dilution or concentration of the components in the fluid. Thus, when the tracer component flow and the sample flow are contacted in a laminar flow, there is substantially no concentration gradient of the components across the fluid flows. In contrast, there is a concentration gradient of the tracer component across the fluid flows, and it is the change in this concentration gradient that is monitored over time.

In certain embodiments of the invention, the method provides the use of two flows of the fluid sample that do not contain the tracer component. These fluid flows may be generated from a single part of the fluid sample or these fluid flows may be generated from two parts of the fluid sample, as described in further detail below. These two flows are provided either side of the tracer component flow.

Tracer Component

The tracer component for use in the methods of the invention is a component whose size is known. The size of the component may be known in the art or it may be determined prior to the use of the component in the methods of the invention. The size of the tracer component may be known from the literature and/or this information may be provided from a commercial supplier of the component.

Alternatively, the size of the tracer component may be determined after the component has been used in the methods of the invention.

The size of the tracer component may be determined (or confirmed) using standard analytical techniques.

A reference to the size of the tracer component may be a reference to the radius, such as the hydrodynamic radius, of the component.

The tracer component used in the method of the invention may have a radius of at least 0.05 nm, at least 0.1 nm, at least 0.5 nm, at least 1 nm, or at least 5 nm.

The tracer component used in the method of the invention may have a radius of at most 10 nm, at most 15 nm, at most 25 nm, at most 50 nm, at most 100 nm, or at most 200 nm, or at most 500 nm.

The tracer component may have a radius in a range with upper and lower limits selected from those given above. For example, the present invention is particularly suitable for use with tracer components having radii in the range 0.5 to 500 nm, such as 0.5 to 200 nm, such as 0.5 to 100 nm, such as 0.5 to 15 nm.

The size of the tracer component may be of a substantially similar size to a component held within the fluid sample.

In one embodiment, the tracer component has a radius that is at least 10%, at least 20%, at least 40% at least 50%, at least 60%, at least 70%, at least 80%, or at least 90% that of the radius of a component in the fluid sample.

In one embodiment, the tracer component has a radius that is at most 100% (i.e. the same as that of the component), at most 150%, at most 200%, at most 500% or at most 1,000% that of the radius of a component in the fluid sample.

The tracer component may have a radius that is in a range selected from the upper and lower limits given above. For example, the tracer component has a radius that is from 10% to 200% that of the radius of a component in the fluid sample.

Where diffusion measurements are to be made for multiple fluid samples having a range of viscosities (or a predicted range of viscosities), it is preferred that a tracer component having a small size is used for all experiments.

As explained above, the methods of the invention allow viscosity to be determined even where the tracer component has a comparable size to a component within the fluid sample.

The tracer components typically have a uniform size amongst their population. Using a substantially homogenous population of tracer particles ensures that the determined viscosity values are accurate.

Thus, in one embodiment, the trace components for use in the invention are substantially monodisperse.

In one embodiment, the tracer component has a size distribution where the standard deviation is less than 15%, less than 10%, less than 5% or less than 1% from the mean.

The size distribution of the tracer component may be known from information supplied by the commercial supplier of the tracer component. The size distribution may also be determined by spectroscopic measurements, including microscopy measurements of a sample population of tracer components.

It is possible to use tracer components having different sizes, where the relative numbers of each of the differently sized tracer components are known. The diffusion profiles of multicomponent mixtures may be resolved, for example through the use of the techniques developed by the present inventors as described in WO 2014/064438. For simplicity, it is preferred that tracer components are used having substantially the same size.

The tracer component may be a dissolved in the fluid sample. However, the present invention may also be used to follow the movement of tracer components that are dispersed within a fluid. Thus, the fluids used in the method may be colloidal, and may be a sol or an emulsion, where the tracer component is the dispersed phase.

The amount of tracer component required to perform an analysis according to the method of the invention is not large, and very small quantities of material may be passed through the microfluidic device. It is also possible to collect the fluid exiting the diffusion channel, and this may be reanalysed.

The method of the invention includes the step of measuring the diffusion of the tracer component across fluid flows. The tracer component may be detectable using standard analytical techniques such as fluorescent spectroscopy, luminescent spectroscopy, UV-vis spectroscopy amongst others.

The tracer component is typically a component that does not or is not expected to react with components within the fluid sample. For this reason the use of proteins as tracer components is to be avoided when measuring the viscosity of biological fluids. There is a risk that a protein tracer would interact with components of the biological fluid (e.g. such as other proteins).

The tracer component may be a molecule, such a polymeric molecule.

The tracer component may be a particle.

In one embodiment, the tracer component is a polymer, such as a polymer particle. The tracer component may be polystyrene, such as a polystyrene particle.

In one embodiment, the tracer component is a dye molecule.

A component may have be labelled, to assist detection. For example, in the exemplary methods described herein fluorescently-labelled polystyrene particles are used as a tracer component.

The tracer component may be chosen for its analytical properties. For example, the tracer may possess detectable functionality that is not present (or not thought to be present) within the sample fluid.

For example, the tracer component may be fluorescently active, and the fluorescent excitation and emission wavelengths may be such as are not typical or expected for the components within the sample fluid. In the present case, tracer components that have fluorescent activity are used to determine the viscosity of bovine serum albumin-containing solutions. The fluorescent activity of the tracer particles is not shared with the bovine serum albumin. Thus, the fluorescent signals detected are associated solely with the tracer component, and not any other component of the sample fluid.

Methods

The present invention may be used to determine the viscosity, such as the relative viscosity, of a fluid sample. The methods of the invention look to measure the diffusion of a tracer component of known size through the fluid sample. The diffusion of the tracer component over time allows the viscosity of the fluid to be determined.

In the methods of the invention a flow of the fluid sample is established. This is the sample flow. A flow of a fluid sample containing a tracer component is also established. This is the component flow. These sample and component flows are brought into contact, and a laminar flow is generated in a diffusion channel. Once the laminar flow is established the diffusion of the component from the component flow into the sample flow is monitored. Thus, the location of the component across one or all of the fluid flows may be determined at different diffusion times. From the measured diffusion profiles of the component, the viscosity of the fluid sample may be determined.

The channel is referred to as a diffusion channel, as it is a fluid channel where the diffusion of the component is permitted and monitored.

The flow rate of each flow is maintained at a substantially constant level during the analysis steps. The analysis may be undertaken only when a stable flow is established in the diffusion channel.

The flow rates used are not particularly limited, and it is not necessary for the flow rates of the sample flow and the tracer component flow to be the same.

The flow rate of the tracer component flow may be altered independently of the flow rate of the sample flow.

In practice, the flow rates are selected to accommodate the diffusion of the component across the fluid flows. The flow rate is selected such that there is sufficient residency time within the flow channel to allow for diffusion of the tracer component to be monitored.

The channel is a part of a fluidic device. The fluidic device is adapted for use with a detector at a plurality of locations in the channel. The channel is in fluid communication with supply channels for the sample flow and the component flow.

In some embodiments, two sample flows are provided on either side of the tracer component flow. The method of the invention may therefore look at the diffusion of the tracer component in the tracer component flow into either or both of the flanking sample fluid flows. The use of two sample fluid flows is advantageous as these may be used to provide a stable balancing pressure across the tracer component flow.

The composition of the two sample flows is identical. Typically the flow rate of the two sample flows is identical.

The methods of the invention are typically performed in flows having a low Reynolds number. For example, the Reynolds number of a flow may be 1 or less, 0.5 or less, 0.1 or less, or 0.05 or less.

The methods of the invention may be performed at or around room temperature, for example 15, 20 or 25° C. Alternatively, the methods of the invention may be conducted at lower temperatures, such as 5 or 10° C., or higher temperatures, such as 35, 40 or 50° C. The method of the invention may also include the step of measuring the temperature of the fluids for use in the invention.

In one embodiment the fluid flow rate of the laminar flow is at least 1, at least 5, at least 10, at least 50, or at least 100 $\mu Lh^{-1}$.

In one embodiment the fluid flow rate of the laminar flow is at most 200, at most 400, at most 500, at most 1,000, at most 2,000 or at most 5,000 $\mu Lh^{-1}$.

In one embodiment, the flow rate of the laminar flow is a value selected from a range having upper and lower values selected from the values above. For example, the flow rate may be in range 5 to 400 $\mu Lh^{-1}$.

The fluid flow rate is the flow rate at steady state.

The laminar fluid flow rate refers to the combined flow rate of the sample flow (or sample flows) and the tracer component flow. The flow rates of the tracer component flow and the sample flow may be adjusted to achieve the desired flow rate in the diffusion channel.

The use of microfluidic devices with flow rates in the range indicated above means that relatively small quantities of component fluid may be used in an analytical run. For example, volumes in the range are sufficient to establish a steady state flow in the diffusion channel for the purposes of obtaining at least one diffusion profile reading.

In one embodiment, the total volume of fluid used in the method is at most 50, at most 100, at most 200, at most 500, or at most 1,000 μL.

In one embodiment, the total volume of fluid used in the method is at least 0.1, is at least 0.5, is at least 1, is at least 5, or is at least 10 μL.

In one embodiment, the total volume of fluid used is a value selected from a range having upper and lower values selected from the values above. For example, the total volume may be in range 1 to 50 μL.

The total volume of fluid refers to the combined volumes of the tracer component fluid and the sample fluid used in the method.

In one embodiment, the lateral diffusion of the tracer component from the tracer component flow into the sample fluid flow is measured at a plurality of diffusion times.

The lateral diffusion may therefore be measures at a plurality of locations along the diffusion channel. The separation between measurement points is not particularly limited, but may be of sufficient distance that the recorded diffusion profiles have noticeably changed between measurement points.

In an alternative embodiment, the lateral diffusion of the tracer component is measured at a single location in the channel. Once the lateral diffusion has been recorded, the flow rates of the tracer component and sample fluid flows are altered, and once a stable flow is established, the lateral diffusion of the tracer component is measured at the single location. Thus, diffusion profiles at different diffusion times may be obtained through changes to the flow rates. The flow rates may be changed one, two, three or more times.

Fluidic Device

The method of the first aspect of the invention makes use of a diffusion channel which is a part of a fluidic device, for example a microfluidic device.

Thus, the fluidic device comprises a diffusion channel. The diffusion channel holds the laminar flow of the tracer component flow with a sample fluid flow, or the diffusion channel holds the laminar flow of the tracer component flow with two sample fluid flows, which are provided either side of the tracer component flow.

The diffusion channel is adapted for use with an analytical device, which is suitable for determining the lateral distribution of a tracer component at one or more locations along the diffusion channel.

The diffusion channel may be in fluid communication with an upstream channel having a larger cross section (a large cross section channel). The diffusion channel may accordingly be referred to as a small cross section channel. The use of large and small cross section channels in a diffusion device is described by the present inventors in WO 2014/064438, the contents of which are hereby incorporated by reference in their entirety.

The use of microfluidic channels to hold the tracer component and sample fluid flows ensures that the flows take place at low Reynolds numbers, and consequently convection and diffusion are the only relevant mechanism of mass transport within the system. Accordingly, this allows accurate numerical calculations to be performed.

The general dimensions of the channels in the device are selected to provide reasonable mobilisation rates and analysis times. The dimensions of the device may also be selected to reduce the amount of fluid required for a sufficient analysis run.

The diffusion channel (and the large cross section channel, where present) is a channel having suitable dimensions allowing for the generation and maintenance of a laminar flow of two (or three) streams within. The laminar flow of two streams means that the flows are side by side and are stable. Thus, there are typically no regions where the fluids recirculate, and the turbulence is minimal. Typically such conditions are provided by small channels, such as microchannels.

Devices for use in dispersive measurements are well known in the art, and are described, for example, by Kamholz et al. (*Biophysical Journal*, 80(4):1967-1972, 2001) and WO 2014/064438.

A reference to a channel herein, such as a diffusion channel, is a reference to a channel having a substantially rectangular cross section. Thus, the channel may be formed of a substantially flat base with walls which extend substantially vertically therefrom, and optionally a top cover. Typically, the base and the walls are formed into a silicone substrate. The cover may be a glass cover, for example a standard glass slide or a borosilicate wafer. The detection apparatus may be provided above the diffusion channel.

A reference to width is a reference to the lateral diffusion dimension in the channel (which is referred to as d in some prior art references).

The diffusion channel has a substantially constant width throughout its length.

The width of the diffusion channel may be at most 500 µm, at most 700 µm, at most 1,000 µm, or at most 2,000 µm.

The width of the diffusion channel may be at least 5 µm, at least 10 µm, at least 50 µm, at least 100 µm or at least 200 µm.

In one embodiment, the width of the diffusion channel may be in a range selected from the upper and lower values given above. For example, the width may be in the range 10 to 500 µm.

The length of the diffusion channel may be of a length suitable to allow the diffusion of the component in the component flow to the channel edge forming the boundary for the sample fluid flow. Thus, by the time the fluid flows have reached the end of the diffusion channel, all the components present in the component flow have reached the maximal entropic configuration.

The length of the diffusion channel is sufficient to allow a tracer component to diffuse from the tracer component fluid flow into the sample fluid flow. For tracer components, such as polymers, having the molecular weights described herein, diffusion channel lengths of 1 mm length or more are generally sufficient.

In one embodiment, the diffusion channel is at least 0.5 mm, at least 1 mm, at least 2 mm, or at least 5 mm long.

In one embodiment, the diffusion channel is at most 10 mm, at most 20 mm, or at most 50 mm long.

In one embodiment, the diffusion channel length may be in a range selected from the upper and lower values given above. For example, the diffusion channel length may be in the range 0.5 to 50 mm, such as 1 to 20 mm.

The flow of the fluids is along the longitudinal axis of the diffusion channel. The diffusion of the tracer component in the tracer component flow into the sample flow is transverse to the longitudinal axis of flow, across the width of the channel.

In some embodiments at least a part of the diffusion channel is convoluted. Thus, the diffusion channel may include a turn or series of turns, for example. The use of a convoluted geometry allows the size of the device to be minimised. The use of a convoluted path may also provide multiple flow channels within a single detection zone. In a single detection zone multiple channels (corresponding to different flow distances and therefore different diffusion times) may pass across a detector allowing multiple and simultaneous measurements to be made.

The diffusion channel may receive the sample and tracer component fluid flows directly from supply channels for each of the sample and tracer component fluids. Thus, the fluid flows contact at a junction of the upstream region of the diffusion channel.

In another embodiment, the diffusion channel may receive the sample and tracer component fluid flow from an upstream large cross section channel.

Fluid exiting from the diffusion channel may be collected for further analysis. Thus, the diffusion channel is in fluid communication with a sample collection reservoir. Alternatively, the diffusion channel may be in fluid communication with a further fluidic device, for example a device for measuring a second physical property of the fluid. In one embodiment, the diffusion channel is upstream of a second analytical device for determining the hydrodynamic radius of a component within the sample fluid (which component may be referred to as an analyte).

The fluidic device may be provided with supply channels providing fluid communication between the reservoir and the diffusion channel, either directly or via a large cross section channel. Where two sample flows are to be provided into the diffusion channel (and either side of the tracer component flow), each of the sample fluid flows may be delivered independently from different reservoirs. However, each of the sample fluid flows may be provided form a single reservoir that is linked to the large cross section channel via two supply channels.

The dimensions of each supply channel are not particularly limited and may be similar to or the same as the diffusion channel. In one embodiment, each supply channel has a width that is greater than the width of the diffusion channel. In one embodiment, each supply channel has a width that is less than the width of the diffusion channel.

Each reservoir may be a syringe which is connected to a supply line of the fluidic device. The syringe may be under the control of a suitably programmed computer which is capable of indecently controlling the flow rate of fluid from the reservoir to the large section channel. The control of such devices is well known in the art.

Alternatively each reservoir may be provided as part of the microfluidic device.

In other embodiments, the flow of fluid from one or more reservoirs may be a gravity feed.

A fluidic device according to the present invention and for use in the methods described herein may be prepared using standard techniques known in the art. Thus, photolithography may be used to generate fluid channels and optionally fluid reservoirs, in an appropriate substrate, such as a silicone substrate. The techniques described in Kamholz et al. (*Biophysical Journal*) may be used with appropriate adaptations to the photolithographic mask to accommodate the introduction of a large cross section channel and additional sample fluid flow channels, where appropriate.

Fluidic channels prepared by photolithographic techniques may be finished by providing fluid access and exit ports, for example by drilling into the substrate to provide access to the relevant channels. Where external reservoirs, such as syringes, are used to supply fluids directly to the large cross section channel or to a supply channel, an appropriate manifold may be used.

The fluidic device may be used in combination with a suitably programmed and programmable computer for controlling the flows into the large cross section channel and for managing the detection device. The computer may also analyse the recorded data and provide real time diffusion values.

The device is suitable for integration with a detector for measuring the lateral diffusion of the one or more components in the diffusion channel.

The diffusion channel depth may be selected to reduce the time scale for analyte diffusion across the channel width (thereby to reduce the time taken to approach the steady state solution). The depth of the channel may be selected so as to minimise or eliminate artefacts that are associated with the deepest channels (see Kamholz et al. *Biophysical*). The depth of the channel may be selected so as to minimise or eliminate loading problems and high fluid resistance that are associated with very shallow channels (ibid.). Where a large cross section channel is present, its depth may be the same as the diffusion channel.

In some prior art references the height or depth of the channel is referred to as the width, w.

The aspect ratio, the ratio of the width of the channel to the height of the channel, may be 100 or less, 50 or less, 25 or less, or 10 or less.

The aspect ratio may be 1 or more, 2 or more, 4 or more, or 5 or more.

In one embodiment, the aspect ratio may be in a range selected from the upper and lower values given above. For example, the aspect ratio may be in the range 5 to 100.

Generally larger aspect ratios, such as 4 or more, are favoured as the fully developed velocity profiles will be parabolic across the channel height and approximately blunt across the channel width (see Kamholz et al. *Biophysical*).

The channel height (or channel depth) of the diffusion channel is not particularly limited, save for the considerations discussed above. Where a large cross section channel is present, the channel height of the large section channels may be the same as the diffusion channel. The channel height is substantially constant throughout the channel.

In one embodiment, the channel height is at least 5 µm, at least 10 µm, or at least 15 µm.

In one embodiment, the channel height is at most 30 µm, at most 50 µm, at most 100 µm, or at most 500 µm.

In one embodiment, the channel height may be in a range selected from the upper and lower values given above. For example, the channel height may be in the range 10 to 50 µm.

Channels known from the prior art typically have a depth in the range 10 to 100 µm (see Kamholz et al.)

As noted above, the depth of the channel may be selected in relation to the width of the channel to provide a suitable aspect ratio.

It is not necessary to separate the laminar flows from each other in order to perform the analytical analysis. The analytical measurement may be recorded across both the component flow and the sample flow.

The device is also provided with a detector for detecting the location of the component in the diffusion channel. This is described in further detail below.

In one embodiment, the fluidic device is provide with a large cross section upstream and in fluidic communication with the diffusion channel. The use of a large cross section is intended to minimise fluid stagnation in the device and minimise the flow development region that extends from the stagnation point, thereby allowing a stable flow to form in a reduced time.

The large section channel is the region where the flow of the tracer component fluid is brought into contact with the flow of the sample fluid. The flows are then directed by the large cross section channel to the diffusion channel. It is in the diffusion channel that the diffusion of the tracer component into the sample flow is monitored.

The large cross section channel is in fluid communication with the diffusion channel. Where a large cross section channel is present, the diffusion channel may be substantially straight and in line with the large cross section channel.

The large section channel may be referred to as a convergent nozzle.

The large cross section channel may have a region of substantially constant maximum width followed downstream by a convergent region where the width of the channel narrows until the width matches that of the diffusion channel.

Alternatively, the large cross section channel may comprise a convergent region only, where the width of the channel narrows from a maximum width until the width matches that of the diffusion channel.

The rate at which the convergent region narrows may be constant.

The precise rate at which the convergent region narrows (the angle of the nozzle) is not particularly limited as the narrowing is usually far removed from the component flow. However, generally the present inventors have found that nozzles having an angle in the range 40° to 70°, such as 50° to 70°, such as 55° to 65°. Here, the angle is with respect to the flow direction of the tracer component flow in the wide cross section channel.

The maximum width, w, of the large cross section channel is greater than the width of the diffusion channel.

In one embodiment there is no section is the large cross section channel that is of a width smaller than the width of the diffusion channel. In one embodiment the minimum width of the large cross section channel is the same as the width of the diffusion channel.

The maximum width, w, of the large section channel may be at most 500 µm, at most 700 µm, at most 1,000 µm, at most 2,000 µm, at most 5,000 µm, or at most 10,000 µm. Generally channel widths of greater than 10,000 µm are not practical, as the material from which the device is made, typically PDMS, is likely to sag.

The maximum width, w, of the large section channel may be at least 50 µm, at least 100 µm, at least 200 µm, or at least 500 µm.

In one embodiment, the maximum width of the large cross section channel may be in a range selected from the upper and lower values given above. For example, the width may be in the range 200 to 5,000 µm, such as 200 to 1,000 µm, or such as 1,000 to 5,000 µm.

The length of the large section channel is at most 500 µm, at most 700 µm, or at most 1,000 µm The length of the large section channel is at least 10 µm, at least 50 µm, at least 100 µm or at least 200 µm.

In one embodiment, the length of the large cross section channel may be in a range selected from the upper and lower values given above. For example, the length may be in the range 50 to 500 µm, such as 100 to 500 µm.

Where the large cross section channel comprises a region of substantially constant maximum width and a downstream region where the width converges to the width of the diffusion channel, the region of substantially constant maximum width may be at least 50%, at least 60%, at least 70%, at least 80% or at least 90% of the total length of the large cross section channel.

In one embodiment, the maximum width of the large section channel is at least 1.2 times, at least 1.5 times, at least 2 times, at least 5 times, or at least 10 times the width of the diffusion channel.

In one embodiment, the maximum width of the large section channel is at most 20 times, at most 50 times, at most 100 times the width of the diffusion channel.

In one embodiment, the maximum width of the large cross section channel in relation to the diffusion channel may be in a range selected from the upper and lower values given above. For example, the maximum width of the large cross section channel may be in the range 5 to 20 times the width of the diffusion channel.

The length of the large section channel is the distance from the point at which the sample and tracer component fluid flows come into contact to the point at which the channel width of the large section channel matches that of the diffusion channel. The diffusion channel receives the sample and tracer component fluid flow from the large cross section channel.

Detection

The methods of the invention include the step of determining the lateral distribution of the tracer component across the diffusion channel. There are no particular restrictions on the way that the diffusion of a tracer component into the sample flow is measured, and the detection method employed may be based on the tracer component to be detected.

The detector is one that is suitable for use with fluidic flow channels, and particularly microfluidic channels. Diffusion detection methods are well known in the art and are described by Kamholz et al. (*Biophysical*), for example. Examples include UV-vis, fluorescent or luminescent spectroscopic methods, amongst others.

The lateral distribution of the tracer component may be determined at one location in the diffusion channel. Here, the measurement of different diffusion times may be achieved by varying the flow rate of the fluids in the diffusion channel.

The distribution of component may be determined at two or more, such as three, four or five, locations along diffusion channel. As noted above, the method may include the step of determining the diffusion profile of the component at a plurality of locations in diffusion channel.

At least one diffusion measurement should be recorded before the tracer component has diffused to the channel edge that is the boundary of the device to the sample fluid flow. It will be appreciated that a small tracer component that will diffuse quickly to the channel edge, whilst a larger tracer component will take more time.

Where multiple diffusion measurements are made along the diffusion channel, the location of each the second and subsequent along the channel is not particularly limited. Typically, the subsequent measurements are taken at sufficiently further distances along the diffusion channel to give diffusion profiles of useful difference to previous measurements.

The methods of the present invention do not require the separation of the sample flow from the component flow. Thus, the diffusion profile of the one or more components may be measured whilst the component flow and the sample flow are in contact.

The tracer component may be selected for its ease of detection. The tracer component may possess functionality in the form of a chemical group that is detectable by standard UV-vis, fluorescent or luminescent spectroscopy, for example.

Viscosity Determination

In the methods of the invention the flow of fluids occurs in the laminar regime. For example, Reynolds numbers are generally in the order of $1\times10^{-7}$. As previously noted, the transport of components within a diffusion channel is governed by convective and diffusion motions only. Such can be readily modelled by the corresponding mass transport equations.

Figure 3:
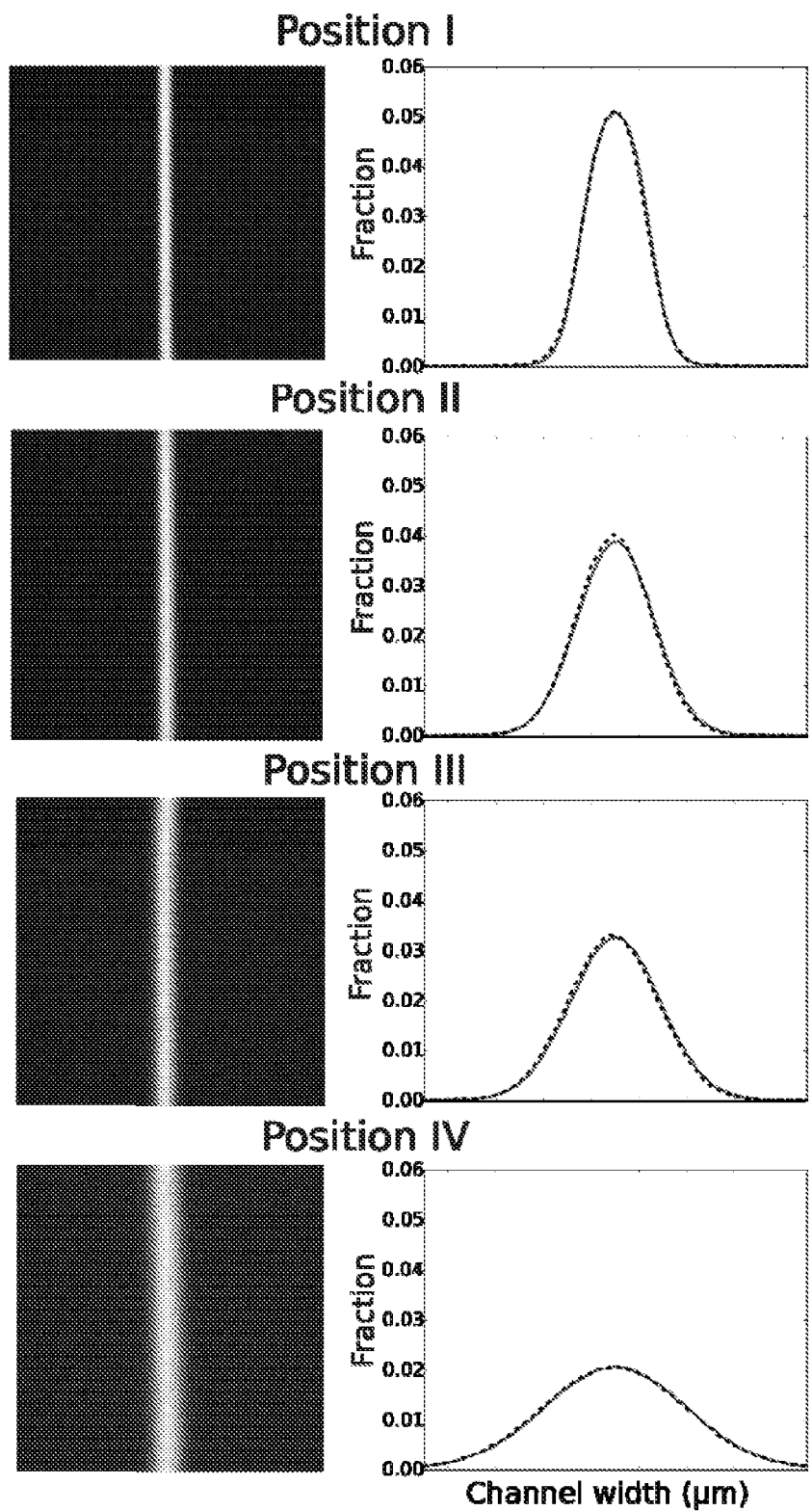
FIG. 3 is a series of images (left) showing the diffusion of particles across the fluid flows in a diffusion channel in the fluidic device of FIGS. 1a and 1 b. Also provided are the diffusion profiles (right) for each of the images, where the profiles include the measured (dotted lines) and simulated (continuous lines) diffusion profiles. The images make use of a 10 wt % glycerol in water solution. Positions I, II, III and IV are located at 5.3 mm, 18.6 mm, 30.4 and 88.7 mm respectively along the diffusion channel.

The comparison between model simulations and experimental data shows that the diffusion coefficient of a tracer component to be determined with high accuracy. A detailed description of model simulations and fitting procedures may be found in Arosio et al. (in press) and also WO 2014/064438, the contents of which are hereby incorporate by reference in their entirety. An example fit of experimental to theoretical data is shown in FIG. 3 of the present case.

The acquisition of a large number of diffusion profiles is advantageous: increasing the information content of diffusion measurements allows a robust estimation of the diffusion coefficient. Thus, in the methods of the invention, the diffusion of the component is measure at a plurality of diffusion times. Typically the diffusion of the component is measured at a plurality of locations along a diffusion channel.

From the apparent diffusion coefficient of a component (D), the viscosity ($\eta$) of a fluid can be calculated according to the Stokes-Einstein relationship as:

$$\eta = \frac{kT}{6\pi R_h D}$$

where T is temperature, k is the Boltzmann constant and $R_h$ is the hydrodynamic radius of the tracer component.

The measurement of viscosity ($\eta$) may refer to the measurement of relative viscosity ($\eta_r$), which is defined as the ratio between the viscosity of a given sample fluid ($\eta$) and the viscosity of pure water ($\eta_0$), such as milli-Q water. The viscosity values may be determined and quoted with respect to the temperature of the sample fluid at the time of the diffusion experiment.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL

Materials

Fluorescent polystyrene nanoparticles with nominal diameters of 47 nm (green) or 100 nm (red) and density of 1.06 kg/dm$^3$ were supplied by ThermoFisher Scientific (UK). Excitation and emission maxima were 468 and 508 nm for the green particles and 542 and 612 nm for the red particles, respectively. Glycerol and bovine serum albumin (BSA) were supplied by Sigma Aldrich (USA). All aqueous solutions were prepared in milli-Q water. The concentration of the probe nanoparticles was 0.05 wt %.

Microfluidic Device

Figure 1B:
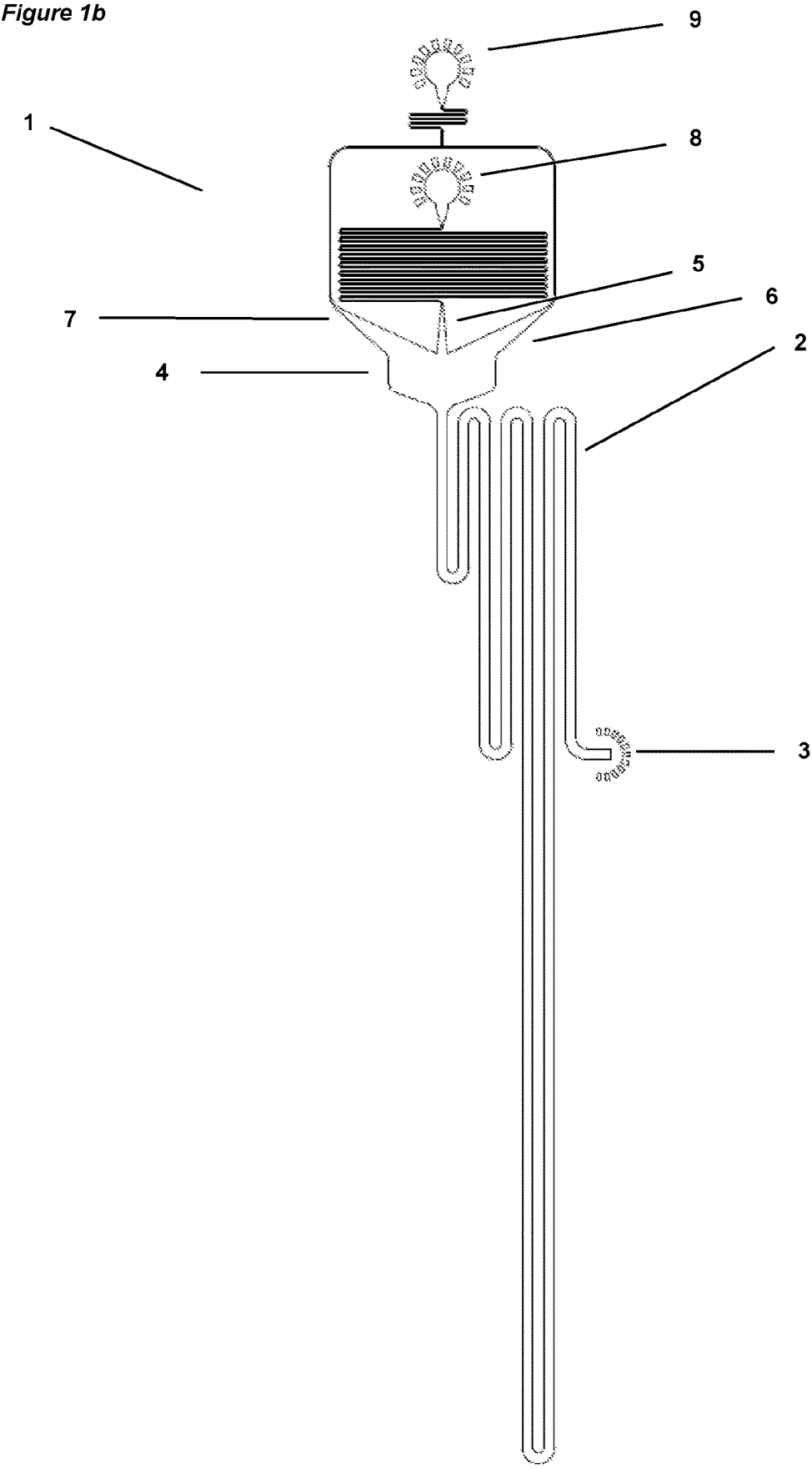

A microfluidic device was prepared according to the design of the device shown in FIGS. 1*a* and 1*b*. FIG. 1*a* shows a part of the device of FIG. 1*b*.

The microfluidic device 1 has a convoluted diffusion channel 2 for holding the laminar flow of the sample flow and the tracer component flow (only part of the diffusion channel is shown in FIG. 1*b*). At the downstream end of the diffusion channel 2 there may be provided a collector 3 to collect fluid sample. The collector 3 may be the reservoir of a syringe pump, for drawing fluid through the device.

Alternatively, the downstream end of the diffusion channel 2 may be in fluid communication with a further microfluidic analytical device.

The diffusion channel 2 is adapted to allow diffusion measurements to be taken at one or more positions along the channel. Where there are multiple positions for recording the diffusion of the tracer component, each position corresponds to a different diffusion time. The position of the tracer component across the channel may be ascertained using standard spectroscopic techniques, including for example fluorescent techniques. The apparatus for determining the position of the tracer component is not shown in FIGS. 1*a* and 1*b*.

Upstream of the diffusion channel 2 is a large cross section channel 4, which has a larger cross section than the diffusion channel. The large cross section channel is tapered to its downstream end where it is in fluid communication with the diffusion channel 2. The large cross section channel 4 may be referred to as a nozzle.

The large cross section channel 4 is in fluid communication with three supply channels 5, 6, 7 which meet at a junction at the upstream end of the nozzle. The large cross section channel 4 is provided in order to establish a stable flow of the tracer component flow and the sample flow. The large cross section channel 4 ensures that there is minimal residency (stagnation) of the tracer component at the junction.

The large cross section channel 4 is provided with a central supply channel 5 for supply of the tracer component flow, and two flanking supply channels 6, 7 either side of the central supply channel 5 for the supply of sample flows.

Upstream of the central supply channel 5 is a reservoir 8 holding the tracer component fluid, which is a part of the sample fluid further comprising a tracer component. Upstream of the flanking supply channels 6, 7 is a common reservoir 9 holding a part of the sample fluid. Alternatively each of the flanking supply channels 6, 7 may be supplied by a separate reservoir, with each holding parts of the sample fluid.

In use, the sample fluids and the tracer component fluids are permitted to flow through their respective supply channels 5, 6, 7 and come into contact at the junction of the large cross section channel 4.

At the junction at the upstream end of the large cross section channel 4, the sample flows are provided either side of the tracer component flow. The flows are permitted to flow downstream into the diffusion channel 2.

The flow of fluids through the device 1 may be controlled by a syringe pump placed at the downstream end of the diffusion channel 2. Thus, the syringe pump may be used to draw fluid through the device from the supply reservoirs 8, 9.

Alternatively each of the reservoirs 8, 9 may be reservoirs of syringe pumps. Thus, each syringe pump may push fluid through the device from the supply reservoirs. Here, the flow rates of the sample flow and the tracer component flow may be independently varied.

A microfluidic device having the design shown in FIG. 1*b* was fabricated by standard soft-lithography technique casting polydimethylsiloxane (PDMS) (Sylgard 184 kit; Dow Corning) on a master wafer, with curing at 65° C. for 75 minutes, peeling off the cured product and bonding it to a glass slide after plasma activation. The channel height was 25 µm. Channel width was 300 µm in the detection region (diffusion channel), 3,000 µm at the nozzle (large cross section channel), and 100 µm in the hydrodynamic resistors (supply channels) introducing buffer and analyte into the nozzle.

The flow in the channel was controlled by applying negative pressure at the outlet by using an external syringe pump (Cetoni neMESYS). The resolution of the technique in a given viscosity range can be readily optimized by controlling the residence time in the channel via tuning the flow rate. The selection of the residence time was optimized in order to have sufficient diffusion transport in the channel to provide significant information on the diffusivity, and at the same time to avoid diffusion of the analyte all the way to the side of the channel, at which point information on diffusion motion is lost.

The fluids were illuminated using a LED light source (Cairn Research) equipped with suitable filter sets (Chroma Technology Corporation, Bellows Falls, Vt., USA) for the specific fluorophore. In particular, the range of excitation and emission were 450-490 nm and 500-550 nm (49002 ET-EGFP) for green nanoparticles, and 624-654 nm and 668-718 nm (49009 ET-Cy5) for the red nanoparticles, respectively. Images were collected at twelve different points along the channel in a range distance from 10 to 100 mm using an inverted microscope (Zeiss Axio Observer D1) equipped with a fluorescent illumination system (Cairn Research OptoLED) and a cooled CCD camera (Photometrics Evolve 512). Typical exposure times were in the range of 0.5-1 s.

Microfluidic Diffusion Measurements

The method of determining sample viscosity was validated using aqueous samples containing varying amounts of glycerol. The viscosity of the samples were determined using the microfluidic device described above and shown schematically in FIG. 1*b*.

Aqueous samples containing from 0 to 50 wt % glycerol were prepared.

The fluids for the sample flow and the tracer component flow were prepared from each aqueous sample. The sample flow was simply a flow of the unmodified sample. The tracer component flow was a flow of the aqueous sample, to which a tracer component had been added (at 0.05%).

The viscosity values were determined from diffusion measurements performed at 20° C. using 47 nm nanoparticles as the tracer component within the tracer component flow. The flow rate for the combined (convective) flow of the sample flow and the tracer component flow in the diffusion channel was 40 µL/h or 5 µL/h for experiments where the glycerol concentrations were smaller or larger than 40 wt %, respectively.

Figure 2:
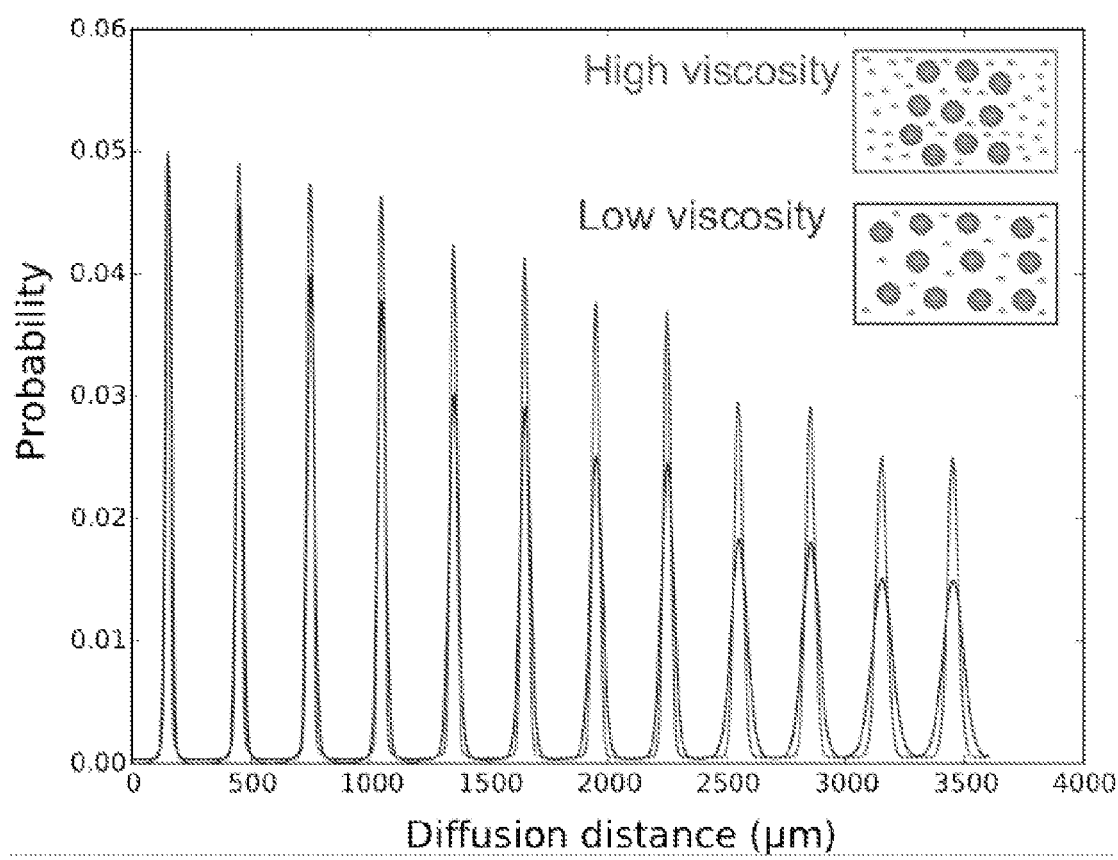
FIG. 2 shows the diffusion profiles for 47 nm particles in 10 wt % (blue) and 50 wt % (red) in aqueous glycerol solutions as measured in the fluidic device of FIGS. 1a and 1b. The diffusion profiles were measured at twelve different diffusion times, at 12 positions along the diffusion channel. The diffusion distance (mm) is the distance from the junctions of the large cross section channel with the diffusion channel. The low and high viscosity samples were 10 wt % and 50 wt % glycerol in water solutions respectively.

The diffusion profiles for the 47 nm nanoparticles were measured at 12 locations along the diffusion channel, at a distance up to around 90 mm from the upstream end of the diffusion channel. Example diffusion profiles are shown in FIG. 2 for aqueous samples containing 10 wt % (blue) and 50 wt % (red) glycerol. As expected, the diffusion of the 47 nm nanoparticles over time is slower for the flows derived from the high viscosity 50 wt % glycerol sample. The diffusion profiles were measured at 3.52 mm, 5.29 mm, 8.57 mm, 10.33 mm, 18.61 mm, 20.37 mm, 28.65 mm, 30.41 mm, 58.69 mm, 60.45 mm, 88.73 mm and 90.5 mm along the diffusion channel from the point at which the large cross section channel converges into the diffusion channel.

FIG. 3 shows images of the diffusion channel at four different locations along the channel. The diffusion of the 47 nm nanoparticles over time is clearly observable as the diffusion of the detectable signal across the image. The diffusion profiles for each of the four images is also shown (solid line in diffusion profiles) together with the simulated diffusion profiles for each of the different diffusion times (dashed line in diffusion profiles). The diffusion profiles were measured at 5.3 mm, 18.6 mm, 30.4 mm and 88.7 mm along the diffusion channel from the point at which the large cross section channel converges into the diffusion channel. A 10 wt % glycerol in water solution was used.

Figure 4:
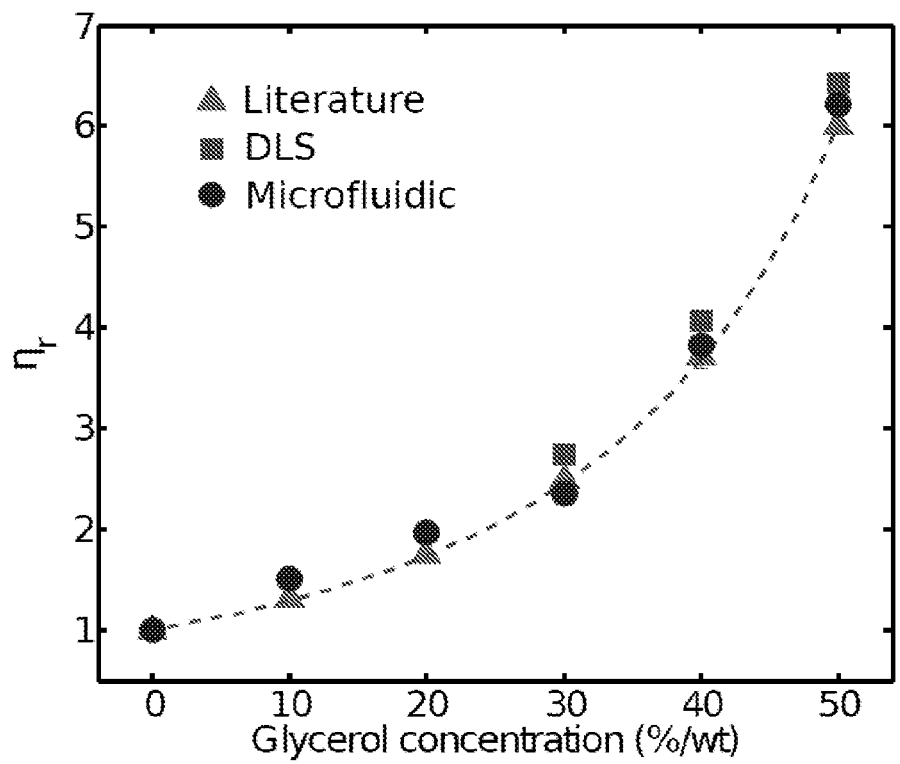
FIG. 4 shows the change in relative viscosity ($\eta_r$) with change in glycerol concentration (mg/mL) in an aqueous sample solution, as measured in the fluidic device of FIGS. 1a and 1b (circles) at 25° C., and by conventional dynamic light scattering technique (squares). The reported literature values are also shown (triangles). The dashed line represents an empirical function reported in the literature.

The increase in the relative viscosity ($\eta_r$) of water-glycerol mixtures with increasing glycerol content is shown in FIG. 4 (as circles). Viscosity measurements of the same samples as determined by dynamic light scattering (squares) are also shown in FIG. 4, along with the literature reported viscosity values reported by Segur et al. (triangles) and the empirically determined viscosity values reported by Cheng (dashed line). The dynamic light scattering are described in further detail below.

The same apparatus and techniques were used to determine the viscosity of solutions having varying concentrations of bovine serum albumin (BSA). Samples containing from 0 to 100 mg/mL BSA were prepared in 20 mM phosphate buffer at pH 7.0. For each of the BSA solutions, measurements were performed at 25° C. using 100 nm nanoparticles, applying a flow rate of 40 μL/h.

As with the glycerol samples, diffusion profiles for the 47 nm nanoparticles were measured at 12 locations along the diffusion channel, at a distance up to around 90 mm from the upstream end of the diffusion channel.

Figure 5:
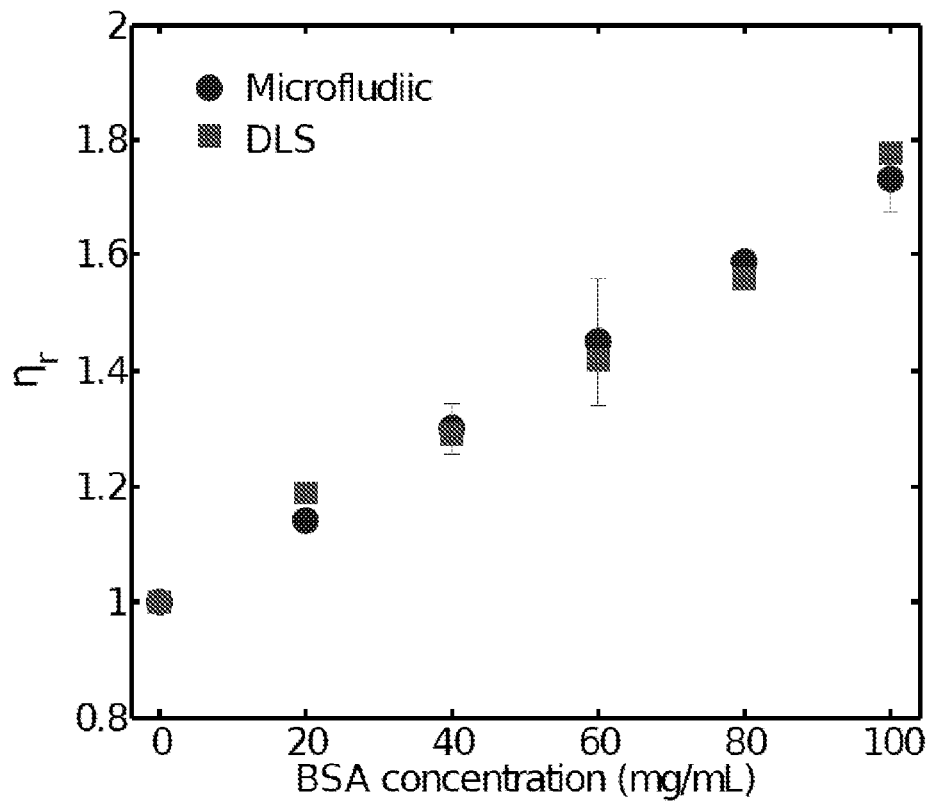
FIG. 5 shows the change in relative viscosity ($\eta_r$) with the change in bovine serum albumin (BSA) concentration (mg/mL) in an aqueous sample solution, as measured in the fluidic device of FIGS. 1a and 1b (circles) using standard nanoparticles of 100 nm diameter at 25° C., and by conventional dynamic light scattering techniques (squares).

The increase in the relative viscosity ($\eta_r$) of water-BSA mixtures with increasing BSA content is shown in FIG. 5 (as circles). Viscosity measurements of the same samples as determined by dynamic light scattering (squares) are also shown in FIG. 5.

From the BSA experiments, it follows that the methods described herein are particularly attractive to measure the viscosity of protein solutions in biotechnological and biological studies.

It will likely be the case that a fluid sample, such as a biological fluid sample, will contain components, such as proteins or aggregates of proteins, that have a similar size to the tracer components used to determine viscosity.

The methods of the invention may be used to determine a sample viscosity and largely regardless of the size of the tracer component and the size of the components within the fluid sample.

The same is not true for dynamic light scattering experiments. In contrast, the presence of components, such as aggregates, having a similar size to the tracer components may compromise the application of techniques based on conventional dynamic light scattering detection.

Figure 6:
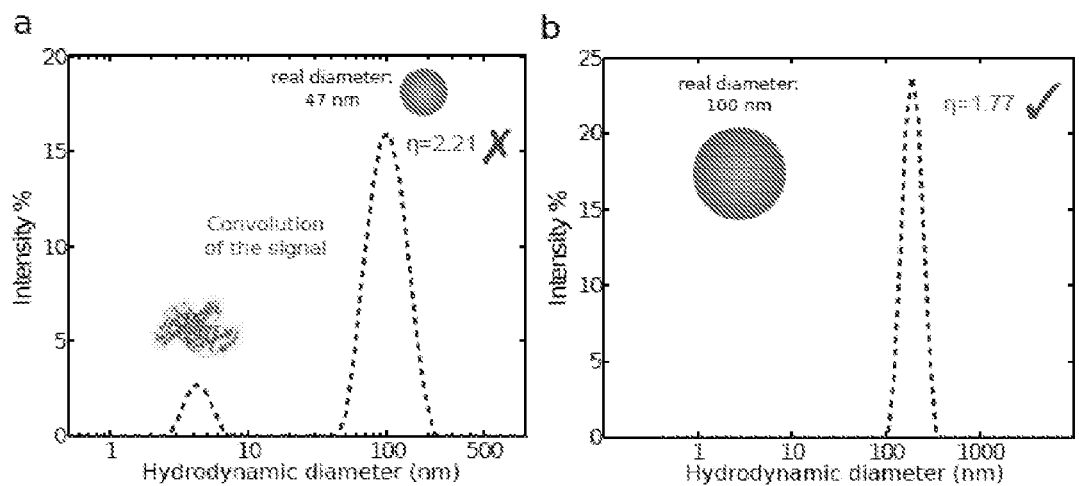
FIG. 6 shows the size distributions (nm) measured by dynamic light scattering for a solution of 100 g/L BSA with 0.05% standard nanoparticles of 47 nm diameter (a) or 100 nm diameter (b).

This can be seen from simple dynamic light scattering intensity experiments for samples containing BSA together with 47 nm or 100 nm particles. Here, the samples contained 100 mg/mL BSA in 20 mM phosphate buffer at pH 7.0, and the particles were provide at 0.05 wt %. The intensity size distribution of each solution was measured by dynamic light scattering. The results are shown in FIG. 6.

When the tracer component is not sufficiently larger than the protein molecules (FIG. 6a), the light scattering signals from proteins and nanoparticles are convoluted. In this case, the accurate sizing of the peak corresponding to the nanoparticles, and therefore the estimation of the solution viscosity, is challenging.

Indeed, the apparent diameter of the nanoparticles as estimated in the intensity size distribution in FIG. 6a is 103.97±0.34 nm, which gives a relative viscosity of 2.21. This differs from the value of 1.73 determined by the methods of the invention and the value of 1.77 determined by dynamic light scattering using larger tracer particles (FIG. 6b).

This limitation can be alleviated by increasing the intensity of the light scattering signal from the tracer component, for instance by increasing either the size or the concentration of the component. However, this optimization procedure can be challenging in the situations where the composition of the solution is unknown.

As noted above, the methods of the invention are largely insensitive to the size of the tracer component and to the composition of the mixture.

Dynamic Light Scattering

Dynamic Light Scattering (DLS) measurements were performed on a Zetasizer Nano instrument (Malvern, UK) working in the backscattering mode at 163°, equipped with a light source with wavelength of 633 nm. The viscosity of water-glycerol mixtures was evaluated by measuring the apparent diffusion coefficient of 47 nm particles, while for BSA solutions 100 nm colloids were considered, since the scattering signal from the 47 nm particles was convoluted with the signal from the protein molecules.

Parallel and Serial Devices

The methods of the invention may be conveniently combined with other fluidic analysis methods. Thus the laminar fluid flow comprising the sample flow and the component flow may be directed to a further microfluidic device after the necessary diffusion profiles have been measured. Thus, the downstream end of the diffusion channel may be in fluid communication with a second fluidic device, such as a second analytical device. The second analytical device may be used to determine a further property of the sample fluid using fluidic techniques.

The present inventors have previously described the use of fluidic techniques to determine the composition of a sample fluid and the size of components within that fluid (see, for example WO 2014/064438), the mass of components within a fluid (see, for example, WO 2015/071681) and the charge-to-size ratio of components within a fluid (see, for example, WO 2015/071683).

For example, the measurement of size of an analyte using fluidic diffusion techniques requires an accurate knowledge of the viscosity of the sample fluid which holds the analyte.

In a preliminary step, the viscosity of a sample fluid may be determined by the methods of the present case. Thus, as explained above, a tracer component is added to a part of the sample fluid and that tracer component is permitted to diffuse into a separate part of the sample fluid.

Subsequently the sample fluid is taken to a second diffusion device where the diffusion of an analyte into the fluid or out of the fluid may be studied. In this way, the size of the analyte, such as the hydrodynamic radius, may be determined.

In one method, the viscosity of the sample fluid is determined without the analyte present. For example, the sample fluid may be a buffer solution containing denaturants or co-solutes at high concentrations. The analyte, such as a protein, may be added to the sample fluid, and the diffusion of that analyte into the sample fluid without the analyte may be measured. The diffusion profiles recoded here permit the size of the analyte to be determined.

Figure 7:
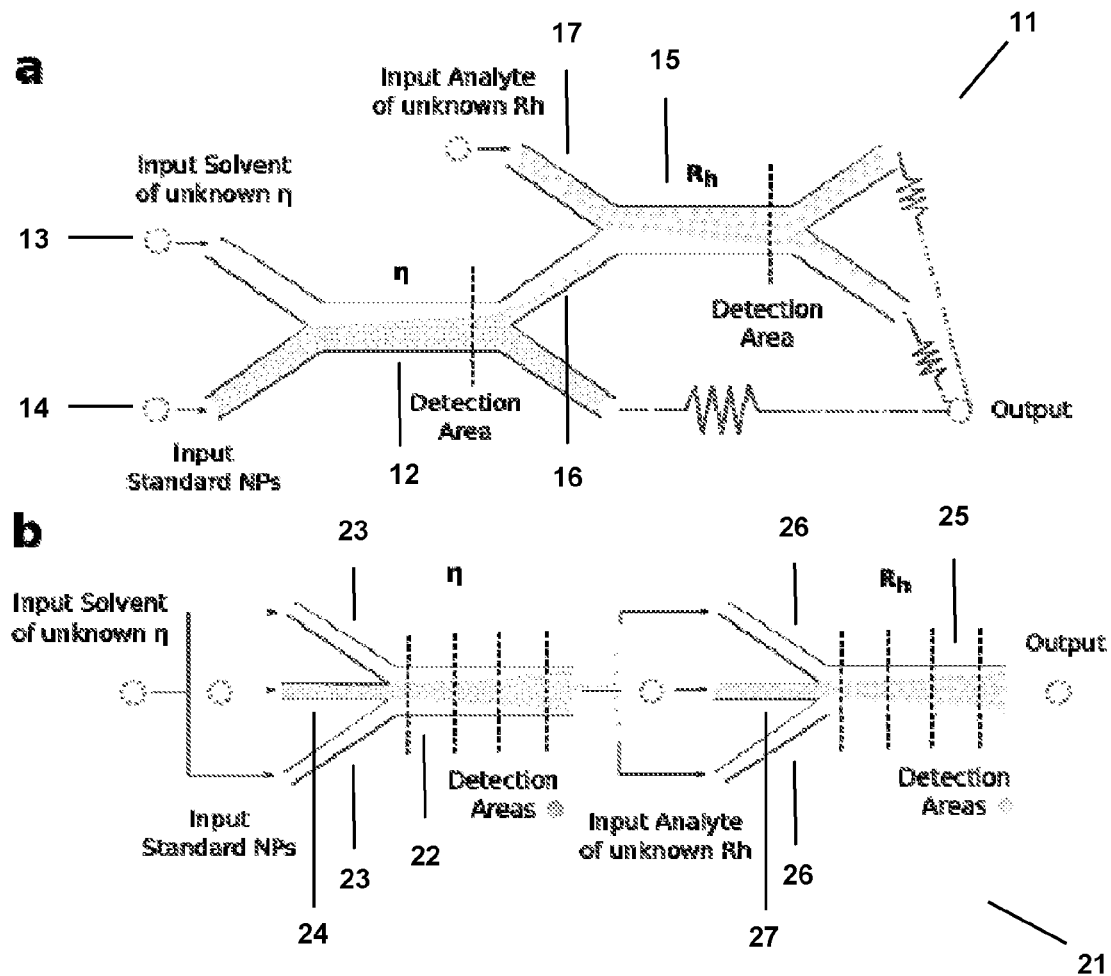
FIGS. 7a and 7b are schematics of fluidic devices for use in a diffusion method according to embodiments of the invention, where (a) is a series device having a 2 channel configuration and (b) is a series device having a 3 channel configuration.

FIG. 7 is a schematic showing the arrangement of two in line fluidic devices. Each device has a first diffusion channel for use in the determination of a fluid sample viscosity, and a downstream second diffusion channel is for determining the size of an analyte added to the fluid sample. A part of the fluid at the downstream end of the diffusion channel is separated and diverted to the diffusion channel of the second device, where it is permitted to contact a fluid sample holding the analyte.

Thus, FIG. 7a shows a fluidic device 11 having a first diffusion channel 12 which is supplied by upstream supply channels 13 and 14. One supply channel 13 supplies a flow of a fluid sample having an unknown viscosity, whilst the second supply channel 14 supplies a flow of the fluid sample which additionally comprises a tracer component of known size, such as a standard nanoparticle. This fluid is the tracer component fluid. The flows of the sample fluid and tracer component fluid are permitted to contact at the upstream region of the diffusion channel 12, and a laminar flow is generated. As the fluid flow passes down the diffusion channel the tracer component is permitted to diffuse from the tracer component flow into the sample fluid flow. The diffusion of the tracer component is measured at one or more locations along the diffusion channel 12. From these measurements the viscosity of the sample fluid may be determined.

At the downstream end of the diffusion channel 12 a part of the laminar flow, such as a part of the sample fluid flow is diverted to a second diffusion channel 15, via a supply channel 16. The second diffusion channel 15 is supplied from by the upstream supply channel 16 and a further supply channel 17, which supplies a flow of a fluid sample having an analyte with an unknown hydrodynamic radius. This latter flow is the analyte flow. The analyte flow and the fluid flow diverted from the first diffusion channel 12 are permitted to contact at the upstream region of the second diffusion channel 15, and a laminar flow is generated. As the fluid flow passes down the second diffusion channel 15 the analyte is permitted to diffuse from the analyte flow into the fluid flow diverted from the first diffusion. The diffusion of the analyte is measured at one or more locations along the second diffusion channel 15. From these measurements the hydrodynamic radius of analyte may be determined.

The device of FIG. 7a is a schematic of a two channel device, where each diffusion channel 12, 15 is provided with two upstream supply channels 13, 14, 16, 17. FIG. 7b is a schematic of a three channel device 21, where each diffusion channel 22, 25 is provided with three upstream supply channels. In a three channel device a laminar flow is generated in the diffusion channel 22, 25, having a central fluid flow with two flanked flows. The component—such as the tracer component or the analyte—whose diffusion is to be studied, is contained within the central flow. The flanking flows contain the sample flow or the analyte flow. A part of the flow from a first diffusion channel 22 is supplied as the central flow for a second diffusion channel 25. As before, the first diffusion channel 22 is for monitoring diffusion for the purpose of determining fluid viscosity, and the second diffusion channel 25 is for monitoring diffusion for the purpose of determining an analyte hydrodynamic radius.

The first diffusion channel 22 is supplied by upstream flanking supply channels 23 and upstream central supply channel 24. The supply channels 23 supply flows of fluid sample having an unknown viscosity, whilst the central supply channel 24 supplies a flow of the fluid sample which additionally comprises a tracer component of known size, such as a standard nanoparticle. The flows of the sample fluid and tracer component fluid are permitted to contact at the upstream region of the diffusion channel 22, and a laminar flow is generated.

As the fluid flow passes down the diffusion channel 22 the tracer component is permitted to diffuse from the central tracer component flow into each of the flanking sample fluid flow. The diffusion of the tracer component is measured at one or more locations along the first diffusion channel 22. From these measurements the viscosity of the sample fluid may be determined.

A part of the laminar flow from the first diffusion channel 22 is diverted to the second diffusion channel 25 via flanking supply channels 26. A central flow containing an analyte of hydrodynamic radius is provided to the second diffusion channel 25 from central supply channel 27. The flows of the diverted sample fluid and the analyte fluid are permitted to contact at the upstream region of the diffusion channel 25, and a laminar flow is generated.

As the fluid flow passes down the diffusion channel 25 the analyte is permitted to diffuse from the central analyte flow into each of the flanking fluid flows. The diffusion of the analyte is measured at one or more locations along the second diffusion channel 25. From these measurements the hydrodynamic radius may be determined.

Figure 8:
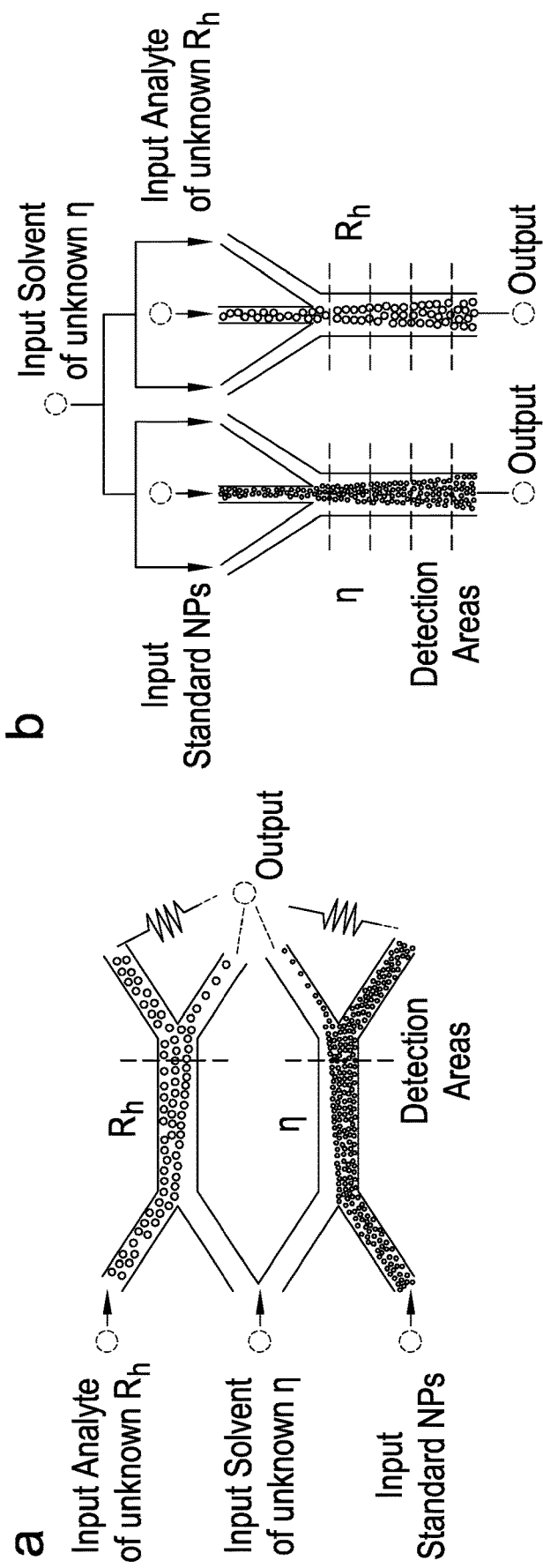
FIGS. 8a and 8b are schematics of fluidic devices for use in a diffusion method according to embodiments of the invention, where (a) is a parallel device having a 2 channel configuration and (b) is a parallel device having a 3 channel configuration.

FIG. 8 is a schematic of fluidic devices for determining the viscosity of a sample fluid and the size of an analyte in parallel. FIG. 8a is a schematic of a two channel device, and FIG. 8b is a schematic of a three channel device.

The experimental set up for the parallel device is similar to that used in the series devices described above. In the parallel device the fluid from one diffusion channel is not diverted into another diffusion channel. The diffusion measurements for viscosity determination and hydrodynamic radius determination are run in parallel. The viscosity measurements are as described above for the tandem device. For the hydrodynamic radius measurements, the sample fluid is not provided from the diffusion channel for viscosity measurements, and is instead supplied directly to the diffusion channel for hydrodynamic radius measurements.

REFERENCES

All documents mentioned in this specification are incorporated herein by reference in their entirety.

WO 2014/064438

WO 2015/071681

WO 2015/071683

M. T. Valentine, P. D. Kaplan, D. Thota, J. C. Crocker, T. Gisler, R. K. Prud'homme, M. Beck and D. A. Weitz, *Physical Review* E, 2001, 64.

Y. Tseng, T. P. Kole and D. Wirtz, *Biophysical Journal*, 2002, 83, 3162-3176.

T. G. Mason, H. Gang and D. A. Weitz, *journal of the Optical Society of America* α-*Optics Image Science and Vision*, 1997, 14, 139-149.

F. He, G. W. Becker, J. R. Litowski, L. O. Narhi, D. N. Brems and V. I. Razinkov, *Analytical Biochemistry*, 2010, 399, 141-143.

A. Palmer, T. G. Mason, J. Y. Xu, S. C. Kuo and D. Wirtz, *Biophysical journal*, 1999, 76, 1063-1071.

A. B. Goins, H. Sanabria and M. N. Waxham, *Biophysical journal*, 2008, 95, 5362-5373.

A. E. Kamholz, B. H. Weigl, B. A. Finlayson and P. Yager, *Analytical Chemistry*, 1999, 71, 5340-5347.

A. E. Kamholz, E. A. Schilling, and P. Yager. *Biophysical Journal*, 80(4):1967-1972, 2001.

J. B. Segur and H. E. Oberstar, *Industrial and Engineering Chemistry*, 1951, 43, 2117-2120.

The invention claimed is:

1. A method for measuring the viscosity of a fluid sample, the method comprising the steps of:
   (i) providing a first flow of the fluid sample;
   (ii) providing a component flow, wherein the component flow is a second flow of the fluid sample further comprising a tracer component;
   (iii) generating a laminar flow of the first flow with the second flow in a diffusion channel, such as a microfluidic diffusion channel;
   (iv) measuring the lateral diffusion of the tracer component across the flows; and
   (v) determining the viscosity of the fluid from the measured diffusion profile, wherein the size of the tracer component is known or is determined.

2. The method of claim 1, comprising the preliminary step of adding a tracer component to a part of the fluid sample.

3. The method of claim 1, wherein step (iv) is measuring the lateral diffusion of the tracer component across the flows at a plurality of diffusion times.

4. The method of claim 1, wherein the tracer component is fluorescent, and the lateral diffusion of the component is measured by fluorescence.

5. The method of claim 1, wherein the channel is a microfluidic channel.

6. The method of claim 1, wherein the first flow and the second flow are brought into contact in a large cross section channel, and the contacting flows are permitted to flow from the large cross section channel into the diffusion channel.

7. The method of claim 1, wherein step (i) further comprises providing a third flow of the fluid sample, and the first and third fluid flows are brought into contact with and provided on opposite sides of the fluid flow comprising the tracer component.

8. The method of claim 1, wherein the component has a radius, such as a hydrodynamic radius, in the range 0.5 to 200 nm, such as 0.5 to 100 nm.

9. The method of claim 1, wherein the component flow is a flow of the fluid sample further comprising a tracer component, and the tracer component is present at 0.2 wt % or less.

10. The method of claim 1, wherein the component is substantially monodisperse.

11. The method of claim 1, wherein the component is a polymeric molecule.

12. The method of claim 1, wherein the fluid sample is an aqueous sample.

13. The method of claim 1, wherein the fluid sample comprises one or more components.

14. The method of claim 13, wherein the fluid sample comprises a component having a polypeptide, polynucleotide or polysaccharide group.

15. The method of claim 13, wherein the fluid sample comprises a component having a radius, such as a hydrodynamic radius, in the range 0.5 to 200 nm, such as 0.5 to 100 nm.

16. The method of claim 13, wherein the tracer component has a radius, such as a hydrodynamic radius, that is from 10% to 200% that of the radius of a component in the fluid sample.

* * * * *